US00PP23368P2

(12) United States Plant Patent
Klemm et al.

(10) Patent No.: US PP23,368 P2
(45) Date of Patent: Jan. 29, 2013

(54) **NEW GUINEA *IMPATIENS* PLANT NAMED 'KLENI10119'**

(50) Latin Name: *Impatiens hawkeri*
Varietal Denomination: KLENI10119

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 37 days.

(21) Appl. No.: 13/136,183

(22) Filed: Jul. 26, 2011

(51) Int. Cl.
*A01H 5/00* (2006.01)

(52) U.S. Cl. ..... Plt./318.5; Plt./318.1

(58) Field of Classification Search ..... Plt./318.1, Plt./318.5
See application file for complete search history.

*Primary Examiner* — Susan McCormick Ewoldt
(74) *Attorney, Agent, or Firm* — Jondle & Associates, P.C.

(57) ABSTRACT

A new New Guinea *Impatiens* plant named 'KLENI10119', particularly distinguished by its suitability for growth in small pots, high density production, very good branching and brilliant petal color, is described.

1 Drawing Sheet

Genus and species: *Impatiens hawkeri.*
Variety denomination: 'KLENI10119'.

BACKGROUND OF THE NEW PLANT

The present invention comprises a new and distinct variety of New Guinea *Impatiens*, botanically known as *Impatiens hawkeri*, and hereinafter referred to by the variety name 'KLENI10119'. The new variety originated from a hybridization made in November 2007 in Kenya. The female parent was the proprietary *Impatiens* plant 'NI-2006-0174' (unpatented), while the male parent was the proprietary *Impatiens* plant 'PTC 1' (unpatented).

The new variety was first propagated in the Summer of 2008 in Stuttgart, Germany and has been asexually reproduced repeatedly by vegetative cuttings in Stuttgart, Germany for 6 generations. 'KLENI10119' has been found to retain its distinctive characteristics through successive asexual propagations.

Plant Breeder's Rights for this variety were applied for in Switzerland on Jun. 23, 2010 and in the European Union on Jul. 9, 2010. 'KLENI10119' has not been made publicly available more than one year prior to the filing of this application.

SUMMARY OF THE INVENTION

The following are the most outstanding and distinguishing characteristics of this new variety when grown under normal horticultural practices in a glass greenhouse in Stuttgart, Germany 1. Suitability for growth in small pots (such as 10.5 cm) and high density production;
2. Very good branching; and
3. Brilliant petal color.

DESCRIPTION OF PHOTOGRAPH

This New Guinea *Impatiens* plant is illustrated by the accompanying photograph which shows the overall plant habit including blooms, buds, and foliage of the plant. The colors shown are as true as can be reasonably obtained by conventional photographic procedures. The photograph is of a plant about 18 weeks old, grown from rooted cuttings in a 10.5 centimeter pot in a glass-covered greenhouse in May 2010 in Stuttgart, Germany, under conditions which approximate those generally used in normal commercial practice.

DESCRIPTION OF THE NEW VARIETY

The following detailed descriptions set forth the distinctive characteristics of 'KLENI10119'. The data which defines these characteristics were collected from asexual reproductions carried out in Stuttgart, Germany. The plant history was taken in June 2010 on 18 week old plants which were planted as rooted cuttings in 10.5 cm pots, and then grown in a glass-covered greenhouse. Color readings were taken under artificial light in the greenhouse. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Balsaminaceae.
- *Botanical name.*—*Impatiens hawkeri.*
- *Common name.*—New Guinea *Impatiens.*

Parentage:
- *Female parent.*—The proprietary New Guinea *Impatiens* plant, 'NI-2006-0174' (unpatented).
- *Male parent.*—The proprietary New Guinea *Impatiens* plant, 'PTC 1' (unpatented).

Growth:
- *Growth and branching habit.*—Compact; round.
- *Height.*—12.0 cm.
- *Width.*—26.0 cm.
- *Propagation.*—Vegetative cuttings.
- *Time from rooted cutting to finish.*—42 days in the Spring when grown in 10 cm pots.
- *Time to initiate and develop roots.*—21 to 28 days.

Branches:
*Average number.*—18.
*Length of branches.*—8.0 cm.
*Internode length.*—2.0 cm.
*Diameter of branches.*—0.6 cm.
*Stem color.*—RHS 145.

Leaves:
*Arrangement.*—Base of the plant: Opposite. Middle and upper section of the plant: Whorled.
*Size.*—Length: 5.2 cm. Width: 2.0 cm.
*Shape.*—Oblong to lanceolate.
*Apex.*—Acuminate.
*Base.*—Acuminate.
*Margin.*—Shallowly serrate.
*Color* (*mature leaves*).—Upper surface: RHS 137A. Lower surface: RHS 138D.
*Color* (*immature leaves*).—Upper surface: RHS 137A. Lower surface: RHS 138D.
*Texture* (*both surfaces*).—Leathery, glossy.
*Venation color.*—Both surfaces: RHS 59C.
*Variegation.*—Absent.
*Petioles.*—Length: 1.0 cm to 2.0 cm. Diameter: 0.2 cm. Color: Upper surface: RHS 130D with RHS 59C (at border). Lower surface: RHS 59C. Texture (both surfaces): Smooth.

Peduncle:
*Color.*—RHS 139D.
*Size.*—Length: 3.7 cm. Diameter: 0.2 cm.
*Texture.*—Smooth.

Flower buds:
*Shape.*—Ovoid, completely closed: drop shaped.
*Size.*—Length: 1.0 cm. Diameter: 0.8 cm.
*Color.*—RHS 59B.

Inflorescence:
*Blooming habit.*—Continuous.
*Inflorescence type.*—Single flower arranged in clusters arising from the leaf axil; flower positioned above the foliage; flowers face upward and outward.
*Number of flowers per node.*—1 to 4 flowers.
*Flowering season.*—April to Fall.
*Lastingness of individual blooms on the plant.*—14 to 21 days.

Flowers:
*Corolla form.*—Single.
*Number of petals.*—5.
*Shape of corolla.*—Round to oval.
*Corolla size.*—Length: 7.0 cm. Width: 6.5 cm. Depth: 0.4 cm.

Petals:
*Shape.*—Cordate.
*Apex.*—Petals are medium incised in the middle.
*Base.*—Round to acute.
*Margin.*—Entire.
*Size.*—Upper petals: Length: 2.2 cm. Width: 3.4 cm. Lateral petals: Length: 3.2 cm. Width: 3.5 cm. Lower petals: Length: 4.0 cm. Width: 3.5 cm. General color description: Red-purple.
*Color.*—Upper surface: RHS 74A. Lower surface: RHS 74B. Eye Zone: RHS 74A.
*Texture* (*both surfaces*).—Satiny, smooth.

Spur:
*Shape.*—Oblong to acute.
*Color.*—RHS 58D.
*Size.*—Length: 5.0 cm to 7.0 cm. Diameter: 0.2 cm. Diameter at proximal end: 0.6 cm. Diameter at distal end: 0.1 cm.

Sepals:
*Quantity per flower.*—3-5.
*Arrangement.*—A large sepal is transformed into the spur. Two of the sepals are clearly separated.
*Lateral sepals.*—Shape: Elliptic acuminate. Length: 0.5 cm. Width: 1.1 cm.
*Lower sepals.*—Shape: Elliptic to round. Length: 1.3 cm. Width: 1.2 cm. Apex: Cuspidate.
*Surface texture* (*both upper and lower surfaces*).—Smooth, glabrous.
*Color* (*both upper and lower surfaces*).—Lateral: RHS 183. Lower: RHS 144A.

Reproductive organs:
*Stamens.*—Number and arrangement: 5 stamens are fused, forming a cap over the ovary. Stamen color (upper surface color): RHS 59D. Anther color: RHS 155B. Pollen color: RHS 155B.
*Pistils.*—Number per flower: 1. Style and stigma: Hair-like. Arrangement: 5 styles and stigmas fused together; arranged in a circle on top of ovary. Color: RHS 59A. Ovary: Shape: Ovate. Length: 0.3 cm to 0.5 cm. Color: RHS 143B.

Fruit and seed set: Seed production has been not observed.

Disease and insect resistance: Plants have medium tolerance to red spider mite.

COMPARISON WITH PARENTAL AND COMMERCIAL VARIETIES

'KLENI10119' differs from the female parent 'NI-2006-0174' (unpatented) by having electric purple colored flowers and very good branching, while 'NI-2006-0174' has violet colored flowers and less branching.

'KLENI10119' differs from the male parent 'PTC 1' (unpatented), by having electric-purple colored flowers, and red-green foliage, while 'PTC 1' has flowers that are red with an outer pink coloring, and green foliage.

'KLENI10119' differs from the commercial New Guinea *Impatiens* variety 'KLENI05080' (U.S. Plant Pat. No. 18,405) by having a more compact growth habit, making it more suitable for growth in a smaller pot (such as 10.5 cm), while 'KLENI05080' has a more vigorous growth, making it more suitable for growth in a larger pot (such as 12.0 cm).

We claim:

1. A new and distinct variety of New Guinea *Impatiens* plant named 'KLENI10119' as shown and described herein.

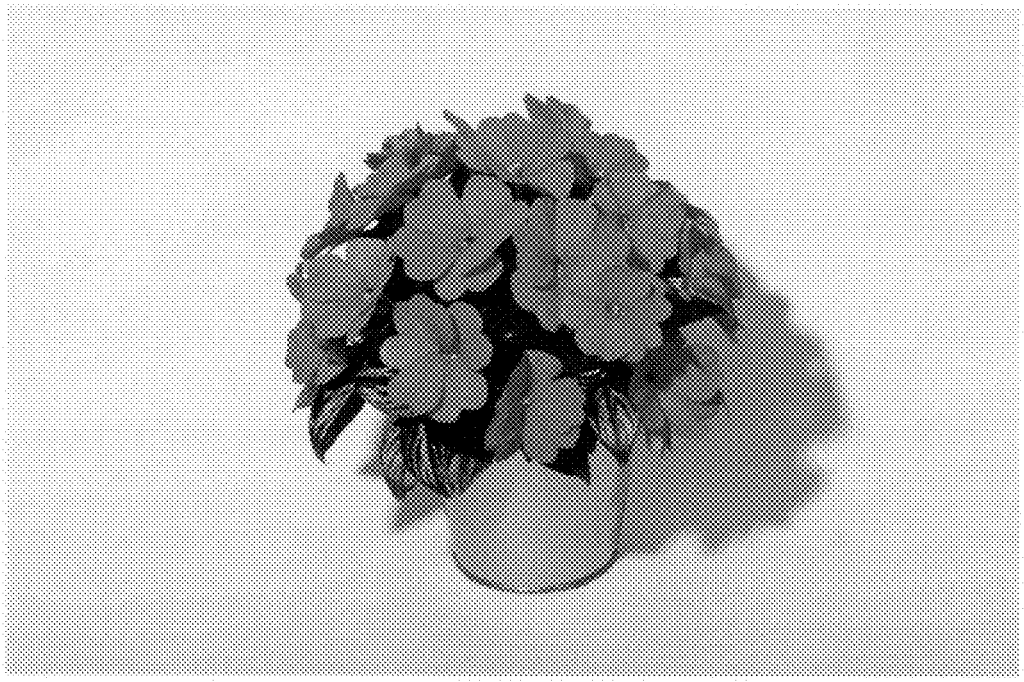

* * * * *